(12) United States Patent
Brindle et al.

(10) Patent No.: US 9,259,490 B2
(45) Date of Patent: Feb. 16, 2016

(54) HYPERPOLARIZED LACTATE CONTRAST AGENT FOR DETERMINATION OF LDH ACTIVITY

(75) Inventors: Kevin Brindle, Cambridge (GB); Mikko Iivari Kettunen, Cambridge (GB); Brett W.C. Kennedy, Cambridge (GB)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

(21) Appl. No.: 13/695,872

(22) PCT Filed: May 2, 2011

(86) PCT No.: PCT/EP2011/056945
§ 371 (c)(1),
(2), (4) Date: Nov. 2, 2012

(87) PCT Pub. No.: WO2011/138269
PCT Pub. Date: Nov. 10, 2011

(65) Prior Publication Data
US 2013/0052141 A1 Feb. 28, 2013

(30) Foreign Application Priority Data
May 3, 2010 (EP) ..................... 10161740

(51) Int. Cl.
*A61K 49/10* (2006.01)
*C12Q 1/32* (2006.01)
*G01N 33/60* (2006.01)

(52) U.S. Cl.
CPC . *A61K 49/10* (2013.01); *C12Q 1/32* (2013.01); *G01N 33/60* (2013.01)

(58) Field of Classification Search
CPC .............................. A61K 31/19; A61K 41/10
See application file for complete search history.

(56) References Cited

U.S. PATENT DOCUMENTS

| | | | |
|---|---|---|---|
| 5,439,803 A | 8/1995 | Ross et al. | |
| 7,256,047 B2 | 8/2007 | Malloy et al. | |

FOREIGN PATENT DOCUMENTS

| | | |
|---|---|---|
| WO | 9830918 A1 | 7/1998 |
| WO | 9858272 A1 | 12/1998 |
| WO | 9924080 A1 | 5/1999 |
| WO | 9935508 A1 | 7/1999 |
| WO | 0196895 A1 | 12/2001 |
| WO | 0236005 A1 | 5/2002 |
| WO | 0237132 A1 | 5/2002 |
| WO | 2006011809 A1 | 2/2006 |
| WO | 2007064226 A2 | 6/2007 |
| WO | 2007/111515 | 10/2007 |
| WO | 2008/020765 | 2/2008 |

(Continued)

OTHER PUBLICATIONS

International Search Report, European Patent Office, dated Aug. 2, 2011.

(Continued)

*Primary Examiner* — Benjamin Packard
(74) *Attorney, Agent, or Firm* — GE Global Patent Operation; Peter T. DiMauro

(57) ABSTRACT

A hyperpolarized MR imaging medium and a method of $^{13}$C-MR detection using a hyperpolarized MR imaging medium for the determination of lactate dehydrogenase (LDH) activity. The contrast media comprises hyperpolarized [$^{13}$C, $^2$H]lactate.

8 Claims, 8 Drawing Sheets

(56) References Cited

FOREIGN PATENT DOCUMENTS

| WO | 2009/013350 A2 | 1/2009 |
|---|---|---|
| WO | 2009/1013350 | 1/2009 |

OTHER PUBLICATIONS

Malaisse, W.J., et al., Generation of L-[2-2H, 2-13 C] lactic acid by erythrocytes exposed to D-[2-13C] glucose in the presence of H2O, Med. Sci. Res. vol. 21, pp. 631-632, 1993.

Malaisse WJ et al., 1993, Medical Science Research, vol. 21, p. 631-2.

Laatikainen R et al., 1996, Magnetic Resonance in Medicine, vol. 36, No. 3, p. 359-65.

Rodrigues TB and Cerdan S, 2005, Magnetic Resonance in Medicine, vol. 54, No. 4, p. 1014-9.

Rodrigues TB et al., 2004, Journal of Neuroscience Research, vol. 79, No. 1 & 2, p. 119-27.

Office Action issued in connection with corresponding CN Application No. 201180022128.2 on May 28, 2014.

Rodrigues et al., "A Fast and Sensitive 1H NMR Method to Measure the Turnover of the H2 Hydrogen of Lactate", Magnetic Resonance in Medicine, Volume No. 54, pp. 1014-1019, Dec. 31, 2005.

Simpson et al., "A PMR Isotope-Exchange Method for Studying the Kinetic-Properties of Dehydrogenases in Intact-Cells", Biochemical Journal, vol. No. 202, Issue No. 3, pp. 573-579, Mar. 15, 1982.

Simpson et al., "Studies of Lactate20 Dehydrogenase in the Purified State and in Intact Erythrocytes", Biochemical Journal, vol. No. 202, Issue No. 3, pp. 581-587, Mar. 15, 1982.

Brindle et al., "A H-NMR Study of the Activity Expressed by Lactate Dehydrogenase in the Human Erythrocyte", European Journal of Biochemistry, vol. No. 158, Issue No. 2, pp. 299-305, 1986.

Yen et al., "Signal Enhancement in Low-Dose Hyperpolarized 13C Imaging Using Multi-Slice FSEPSI Sequence", In Proc Intl Soc Mag Res Med, Toronto, Canada, vol. No. 16, pp. 890, 2008.

Chen et al., "Feasibility of Using Hyperpolarized [1-C-13]Lactate as a Substrate for in Vivo Metabolic C-13 MRSI Studies", Magnetic Resonance Imaging, vol. No. 26, Issue No. 6, pp. 721-726, Jul. 2008.

Albers et al. "Hyperpolarized 15 13C Lactate, Pyruvate, and Alanine: Noninvasive Biomarkers for Prostate Cancer Detection and Grading", Cancer Res, vol. No. 68, Issue No. 20, pp. 8607-8615, Oct. 15, 2008.

Kettunen et al., "Magnetization Transfer Measurements of Exchange Between Hyperpolarized [1-13C]Pyruvate and [1-13C]Lactate in a Murine Lymphoma", Magn Reson Med, vol. No. 63, Issue No. 4, pp. 872- 880, Apr. 2010.

Figure 1A and 1B: Splitting of the $^{13}$C resonance of [1-$^{13}$C]lactate due to $^1$H coupling to the C2 and C3 protons (A). Substitution of the C2 proton with deuterium leaves only the spin-spin coupling to the C3 protons (B). Spin-spin coupling between the $^{13}$C and the C2 deuteron is evidently too small to observe in these relatively low resolution spectra.

The initial pulse was either a 90° pulse, for experiments with non-polarized material, or a low flip angle pulse for experiments with hyperpolarized L-[1-$^{13}$C]lactate. CS indicates a chemical shift-selective pulse and HS indicates a hyperbolic secant pulse.

Hetero-nuclear $^{13}C/^{1}H$ double echo spectra were acquired using a 10 μs 90° $^{13}C$ pulse, a 5 ms adiabatic 180° $^{13}C$ pulse (bandwidth ~2kHz) and a 10 ms adiabatic $^{1}H$ pulse (bandwidth ~1 kHz), which was centred on either the C2 or C3 lactate proton resonances.

Plot of hyperpolarised L-[1-$^{13}$C]lactate signal intensity versus time *in vivo*.

A typical decay curve from a multi-echo experiment in vivo, which was used to estimate $T_2$ values for the lactate, pyruvate and pyruvate hydrate resonances.

The contribution of different $T_2$-components to lactate signal as a function of echo time in vivo.

HYPERPOLARIZED LACTATE CONTRAST AGENT FOR DETERMINATION OF LDH ACTIVITY

CROSS REFERENCE TO RELATED APPLICATIONS

This is a national stage application under 35 U.S.C. §371 (c) of prior-filed, co-pending PCT patent application serial number PCT/EP2011/056945, filed on May 2, 2011, which claims priority to European Patent Application No. 10161740.5, filed on May 3, 2010, the entire contents of which are incorporated herein by reference.

BACKGROUND OF THE INVENTION

Embodiments of the present invention relate to a new hyperpolarized imaging agent and to a method of $^{13}$C-MR detection, which can be used to determine lactate dehydrogenase (LDH) activity.

Previous studies have demonstrated that hyperpolarized [1-$^{13}$C]pyruvate metabolism can be imaged in vivo using $^{13}$C magnetic resonance spectroscopic imaging ($^{13}$C MR imaging). For example WO2006/011809 discloses compositions comprising $^{13}$C pyruvate and methods for using this in $^{13}$C MR imaging.

In tumours, measurements of lactate dehydrogenase (LDH)-catalyzed flux of hyperpolarized $^{13}$C label between pyruvate and lactate have been correlated with tumour grade and response to treatment, see e.g. Albers, M. J., et al. Hyperpolarized $^{13}$C lactate, pyruvate, and alanine: noninvasive biomarkers for prostate cancer detection and grading. *Cancer Res* 68, 8607-8615 (2008). Magnetisation transfer measurements in vivo and studies in tumour cell suspensions in vitro have demonstrated unequivocally that isotope exchange between pyruvate and lactate, as opposed to net chemical flux, makes a significant contribution to the observed flux of hyperpolarized $^{13}$C label between pyruvate and lactate. This is consistent with the long standing observation that LDH catalyses a reaction that is near-to-equilibrium in the cell and that the mechanism of the enzyme is an ordered ternary complex mechanism, in which the coenzymes NAD+ and NADH bind before pyruvate and lactate respectively. Hence, LDH catalyzes the readily reversible interconversion of pyruvate and lactate with concomitant interconversion of NADH and NAD+, as shown in Scheme 1 below.

Scheme 1:

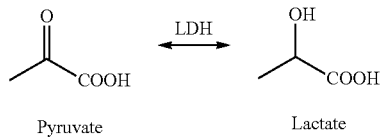

Pyruvate is an excellent hyperpolarized substrate for measuring LDH-catalysed flux since it is non-toxic, it polarizes readily to high levels, the polarization is relatively long-lived and transport into the cell is fast. However, pyruvate has a number of important limitations. While it is an endogenous molecule that has shown no evidence of toxicity at the relatively high concentrations used for hyperpolarized $^{13}$C imaging experiments in vivo, and in an embodiment lactate is used to measure LDH-catalysed flux, since lactate is present naturally at much higher concentrations than pyruvate and is also transported into the cell very rapidly. A further drawback of using labelled pyruvate to measure LDH activity is that the enzyme is inhibited by the high pyruvate concentrations used for hyperpolarized $^{13}$C imaging experiments. However, attempts to use lactate have been relatively unsuccessful since very little label is detected in pyruvate. This is likely because the steady state pyruvate concentration in tissue is very low and therefore there is only a small pool for the hyperpolarized $^{13}$C label in lactate to exchange into.

Both Simpson, R. J., Brindle, K. M., Brown, F. F., Campbell, I. D. & Foxall, D. L. A pmr isotope-exchange method for studying the kinetic-properties of dehydrogenases in intact-cells. *Biochemical Journal* 202, 573-579 (1982), and Simpson, R. J., Brindle, K. M., Brown, F. F., Campbell, I. D. & Foxall, D. L. Studies of lactate-dehydrogenase in the purified state and in intact erythrocytes. *Biochemical Journal* 202, 581-587 (1982) describe LDH-catalysed exchange of isotope label between pyruvate and lactate. $^{1}$H MRS was used in these experiments to measure exchange of methyl deuterated pyruvate ([3-$^{2}$H$_{3}$]pyruvate) with protonated lactate in human erythrocyte suspensions. Following addition of methyl deuterated pyruvate and protonated lactate to an erythrocyte suspension, there was an increase in the methyl proton signal from pyruvate and a corresponding decrease in the methyl proton signal from lactate, as deuterium label was exchanged between the two molecules.

Pyruvate inhibition of LDH in these $^{1}$H MRS experiments with [3-$^{2}$H$_{3}$]pyruvate and protonated lactate was addressed subsequently by instead of measuring label exchange between pyruvate and lactate, exchange of deuterium label was measured between the C2 position of two different isotopically-labelled lactate species, which were distinguished by their methyl label ($^{1}$H or $^{2}$H) (Brindle, K. M. et al. A $^{1}$H NMR study of the activity expressed by lactate dehydrogenase in the human erythrocyte. *Eur. J. Biochem.* 158, 299-305 (1986). This experiment used a spin echo pulse sequence with τ=½J, where J is the $^{1}$H-$^{1}$H coupling constant between the lactate methyl and C2 protons (7.4 Hz) and τ is the delay between the 90 and 180° pulses (68 ms). Under these conditions the lactate methyl resonance is fully inverted in the resulting spectrum. Exchange of the lactate C2 proton for deuterium (D) removes the proton coupling and the phase modulation of the methyl resonance, which now assumes a positive phase. Thus the protonation state of the lactate C2 carbon can be detected via phase modulation of the spin-coupled methyl protons in a homonuclear $^{1}$H spin echo experiment. For example, if an equimolar mixture of perdeuterated and protonated lactate is added to a solution containing lactate dehydrogenase and NAD+ then the $^{1}$H spectrum will initially show an inverted methyl resonance from the protonated lactate. Following LDH-catalysed exchange of deuterium label at the C2 position between the protonated and deuterated lactate species there will be, at isotopic equilibrium, a mixture of the following lactate species: [3-$^{2}$H$_{3}$, 2-$^{2}$H$_{1}$]lactate, [3-$^{2}$H$_{3}$, 2-$^{1}$H$_{1}$]lactate, [3-$^{1}$H$_{3}$, 2-$^{2}$H$_{1}$]lactate and [3-$^{1}$H$_{3}$, 2-$^{1}$H$_{1}$]lactate. Only the methyl protonated species are observed, and of these half will have a proton at the C2 position, and thus the methyl resonance will be inverted, and half will have a deuterium at the C2 position, and thus the methyl resonance will have positive phase. These methyl proton resonances will add to give no signal (there is a slight deuterium shift and thus the signals do not cancel completely). The same experiment can be performed starting with [3-$^{1}$H$_{3}$, 2-$^{2}$H$_{1}$]lactate and [3-$^{2}$H$_{3}$, 2-$^{1}$H$_{1}$]lactate. In this case the observed lactate methyl resonance initially has positive phase, due to the C2 deuteron, and this decays to zero following label exchange at the C2 position.

It has now surprisingly been found that experiments using hyperpolarized [1-$^{13}$C]lactate, in which exchange of $^2$H label between hyperpolarized [1-$^{13}$C, 2-$^2$H$_1$]lactate and endogenous unlabelled lactate in a tissue is monitored, can be performed. Embodiments of the present invention propose the use of hyperpolarized [1-$^{13}$C, 2-$^2$H$_1$]lactate, or other double-labelled isotopomers, to measure LDH activity, where the protonation state of the lactate C2 carbon is detected via phase modulation of the spin-coupled hyperpolarized $^{13}$C label at C1, or at other lactate carbons, in a heteronuclear $^{13}$C/$^1$H spin echo experiment.

There are disorders indicated by elevated LDH, such as various types of cancer.

Hence, there is a need for new improved methods to determine LDH activity, especially LDH activity in vivo.

BRIEF SUMMARY OF THE INVENTION

According to an embodiment of the present invention, there is provided a method for determining LDH activity by $^{13}$C-MR detection. The method comprises using an imaging medium comprising hyperpolarised [$^{13}$C, $^2$H]lactate, and measuring the LDH-catalyzed exchange of deuterium label between the [$^{13}$C, $^2$H]lactate and endogenous unlabelled lactate.

According to an embodiment of the present invention, there is provided a MR imaging medium comprising a [$^{13}$C, $^2$H]lactate isotopomer.

BRIEF DESCRIPTION OF THE DRAWINGS

The accompanying drawings illustrate exemplary embodiments, wherein.

DETAILED DESCRIPTION OF THE INVENTION

Figure 1A:
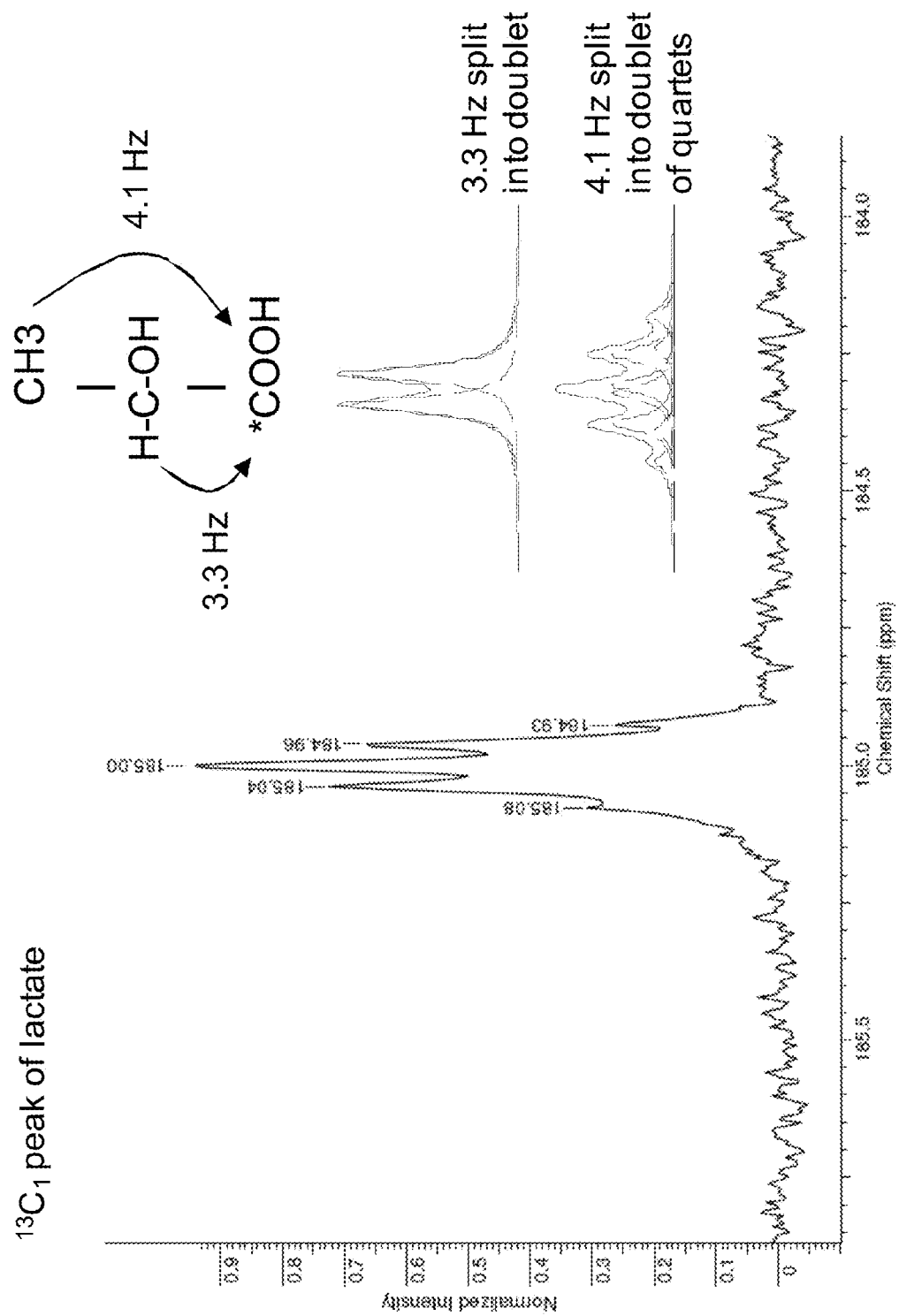
FIG. 1A illustrates a $^{13}$C spectrum of L-[1-$^{13}$C]lactate, and 1B illustrates the spectrum following substitution of the C2 proton for a deuteron according to an embodiment of the present invention.

We describe here a contrast agent and a method for imaging LDH activity which avoids the use of pyruvate by measuring LDH-catalysed exchange of deuterium label between [1-$^{13}$C, 2-$^2$H]lactate and endogenous unlabelled lactate. It has hence been found that hyperpolarised [$^{13}$C, $^2$H]lactate can be used as an agent for determining LDH activity in vivo and in vitro by using $^{13}$C-MR detection. Scheme 2 shows how lactate with a deuterium label in the C2 position is metabolised to protonated (unlabelled) lactate. The C1 position may be $^{13}$C enriched, and is then the position which is hyperpolarized. The $^{13}$C label can also be placed in the C2 or C3 positions, where it will also show spin-spin coupling with the C2 proton. The lactate methyl (C3) protons could also be exchanged for deuterium so that there is only spin-spin coupling between the C2 proton and the $^{13}$C at the C1, C2 or C3 positions.

Scheme 2:

$$\underset{D \quad 1}{\overset{OH}{\underset{2}{\bigwedge}}}\text{COOH} \xrightarrow{LDH} \underset{H \quad 1}{\overset{OH}{\underset{2}{\bigwedge}}}\text{COOH}$$

It has been found that the metabolic conversion of hyperpolarised [$^{13}$C, $^2$H]lactate (i.e. $^{13}$C-deuterium labelled lactate), into hyperpolarised [$^{13}$C, $^1$H]lactate (i.e. $^{13}$C-protonated lactate), could be used to study metabolic processes in the human and non-human animal body using MR. The conversion of hyperpolarised $^{13}$C-deuterium labelled lactate into hyperpolarised $^{13}$C-protonated lactate has been found to be fast enough to allow signal detection from the deuterated $^{13}$C-lactate parent compound and its protonated product. The measured LDH-catalysed exchange of deuterium label between $^{13}$C-deuterium labelled lactate and endogenous unlabelled lactate should be dependent on the metabolic status of the tissue under investigation. The MR signal intensity of hyperpolarised $^{13}$C-lactate is related to the concentration of this species and the degree of polarisation left at the time of detection, hence by monitoring the conversion of hyperpolarised $^{13}$C-deuterium labelled lactate into hyperpolarised $^{13}$C-protonated lactate it is possible to study LDH activity in vivo in the human or non-human animal body by using non-invasive MR imaging or MR spectroscopy.

Thus, an aspect of the present invention provides an imaging medium comprising hyperpolarised [$^{13}$C, $^2$H]lactate. Such isotopically labelled molecules generally named [$^{13}$C, $^2$H]lactate are selected from the group of [1-$^{13}$C, 2-$^2$H]lactate, [2-$^{13}$C, 2-$^2$H]lactate, [3-$^{13}$C, 2-$^2$H]lactate, [1-$^{13}$C, 2,3-$^2$H]lactate, [2-$^{13}$C, 2,3-$^2$H]lactate and [3-$^{13}$C, 2,3-$^2$H]lactate, or from a group of molecules wherein more than one of the C1, C2 and C3 positions are $^{13}$C labelled and wherein the C2 position, or the C2 and C3 positions, are deuterium labelled. According to an embodiment of the present invention, there is provided an imaging medium comprising [1-$^{13}$C, 2-$^2$H]lactate, and particularly, according to an embodiment, hyperpolarised [1-$^{13}$C, 2-$^2$H]lactate.

Lactate is an endogenous compound and its concentration in human blood is relatively high (1-3 mM) with local concentrations of 10 mM and more. Hence, lactate should be very well tolerated and therefore using hyperpolarised [$^{13}$C, $^2$H]-lactate, as an imaging agent is advantageous from a safety perspective.

An aspect of the present invention provides a method of determining LDH activity by $^{13}$C-MR detection using an imaging medium comprising hyperpolarised [$^{13}$C, $^2$H]lactate, wherein the LDH-catalysed exchange of deuterium label between [$^{13}$C, 2H]lactate and endogeneous unlabelled lactate is measured.

In an embodiment of the present invention, the LDH-catalysed exchange of deuterium label at the C2 position between [1-$^{13}$C, 2-$^{2}$H]lactate, or other $^{2}$H and $^{13}$C-labeled lactate isotopomers that are deuterium labelled at the C2 position, and endogenous unlabelled lactate is measured.

The LDH activity measured in cells and tissues by the method of the present invention is an apparent activity since this is dependent on the rate of lactate transport into the cell and the endogenous lactate concentration as well as the LDH activity. In vivo this rate may also depend on the rate of labelled lactate delivery to the tissue under study.

The term "determining LDH activity" denotes measurement of the rate exchange of the C2 deuterium label with proton in hyperpolarised [1-$^{13}$C, 2-$^{2}$H]lactate, or other $^{2}$H and $^{13}$C-labeled lactate isotopomers that are deuterium labelled at the C2 position, and is dependent on the rate of lactate transport into the cell, the endogenous lactate concentration and LDH activity. In vivo this rate may also depend on the rate of labelled lactate delivery to the tissue under study.

In an embodiment of the method according to the present invention the protonation state of the lactate C2 carbon is detected via phase modulation of the spin-coupled hyperpolarized $^{13}$C label at C1, or at other lactate carbons, in a heteronuclear $^{13}$C/$^{1}$H spin echo experiment.

The term "$^{13}$C-MR detection" denotes $^{13}$C-MR imaging or $^{13}$C-MR spectroscopy or combined $^{13}$C-MR imaging and $^{13}$C-MR spectroscopy, i.e. $^{13}$C-MR spectroscopic imaging. The term further denotes $^{13}$C-MR spectroscopic imaging at various time points.

The term "imaging medium" denotes a liquid composition comprising hyperpolarised [$^{13}$C, $^{2}$H], such as [1-$^{13}$C, 2-$^{2}$H] lactate, or other $^{2}$H and $^{13}$C-labeled lactate isotopomers that are deuterium labelled at the C2 position, as the MR active agent, i.e. imaging agent.

The imaging medium used in the method of the present invention may be used as an imaging medium for in vivo $^{13}$C-MR detection, i.e. in living human or non-human animal beings. Further, the imaging medium used in the method of the present invention may be used as an imaging medium for in vitro $^{13}$C-MR detection, e.g. in cell cultures, body samples such as blood or cerebrospinal fluid, ex vivo tissue, for instance ex vivo tissue obtained from a biopsy or isolated organs, all of those derived from a human or non-human animal body.

The terms "lactate" and "lactic acid", according to embodiments of the present invention, denote the L-isomer (L-lactate, L-lactic acid), since this is the isomer used specifically by the mammalian LDH isoforms. The D-isomer (D-lactate, D-lactic acid) is used by microbial lactate dehydrogenases and therefore the D isomers of the labelled lactate isotopomers described above could be used to detect the presence of bacterial infection in a mammalian tissue. Therefore the imaging medium according to the present invention may thus comprise hyperpolarised $^{13}$C-L-lactate or hyperpolarised $^{13}$C-D-lactate, depending on whether the intention is to detect mammalian or microbial LDH activity respectively.

The isotopic $^{13}$C enrichment of the lactate isotopomers used in the method according to an embodiment of the present invention is at least 75%, in an embodiment is 80% and in an embodiment is at least 90%, in an embodiment an isotopic enrichment is over 90%. According to an embodiment the enrichment is 100%. $^{13}$C-lactate used in the method of the present invention may be isotopically enriched at the C1-position (denoted [1-$^{13}$C]lactate), at the C2-position (denoted [2-$^{13}$C]lactate), at the C3-position (denoted [3-$^{13}$C]lactate), at the C1- and the C2-position (denoted [1,2-$^{13}$C]lactate), at the C1- and the C3-position (denoted [1,3-$^{13}$C]lactate), at the C2- and the C3-position (denoted [2,3-$^{13}$C]lactate) or at the C1-, C2- and C3-position (denoted [1,2,3-$^{13}$C]lactate). According to an embodiment, isotopic enrichment is at the C1-position since [1-$^{13}$C]lactate has a longer $T_1$ relaxation in human blood at 37° C. than $^{13}$C-lactate which is isotopically enriched at other C-positions.

The isotopic $^{2}$H enrichment of the lactate used in the method according to an embodiment of the present invention is at least 75%, in an embodiment is at least 80% and in an embodiment is at least 90%, in an embodiment an isotopic enrichment is over 90%. According to an embodiment the enrichment is 100%. Lactate used in the method of the present invention is isotopically deuterium enriched at the C2 position or at the C2 position and the C3 position.

In an embodiment, the imaging medium according to the present invention comprises hyperpolarised sodium $^{13}$C-lactate, and in an embodiment comprises sodium[1-$^{13}$C, 2-$^{2}$H]lactate or the other $^{2}$H and $^{13}$C-labeled lactate isotopomers that are deuterium labelled at the C2 position.

In the preparation of a imaging medium according to the present invention comprising hyperpolarised [1-$^{13}$C, 2-$^{2}$H]lactate, sodium [1-$^{13}$C$_1$]lactate could be used as a starting material as this is a commercially available compound.

For the deuterium labelling, i.e. preparation of [1-$^{13}$C$_1$, 2-$^{2}$H$_1$]lactate, sodium L-[1-$^{13}$C$_1$]lactate is dissolved in $^{2}$H$_2$O. The pH is adjusted by adding an appropriate buffer, such as a phosphate buffer. Other relevant buffers are ACES, PIPES, imidazoles,/HCl, BES, MOPS, HEPES, TES, HEPPS OR TRICIN. Further, chelating agents such as EDTA (ethylenediaminetetraacetic acid) or DTPA may be included in the prepared composition to sequester metal ions from the solution. In an embodiment, EDTA is included. The process step is further outlined in Example 1. Lipoamide dehydrogenase, in this example from pig heart, catalyses exchange of the proton at the C4 position in the nicotinamide ring of NADH with solvent deuterium. This deuterium is then exchanged with the C2 proton in L-[1-$^{13}$C$_1$]lactate in the reaction catalysed by LDH. This coupled enzyme reaction ensures that the proton at the C2 position of L-[1-$^{13}$C$_1$]lactate exchanges with the much larger pool of deuterons in the solvent $^{2}$H$_2$O.

Hence, in one aspect the present invention provides a process for preparation of hyperpolarised [1-$^{13}$C, 2-$^{2}$H]lactate, including the steps of:

i) deuterium labelling sodium [1-$^{13}$C$_1$]lactate to produce [1-$^{13}$C$_1$, 2-$^{2}$H$_1$]lactate, ii) hyperpolarising [1-$^{13}$C$_1$, 2-$^{2}$H$_1$]lactate.

The terms "hyperpolarised" and "polarised" are used interchangeably hereinafter for polarisation of the $^{13}$C-nuclei and denote a nuclear polarisation level in excess of 0.1%, in some embodiments in excess of 1% and in some embodiments in excess of 10%.

The level of polarisation may for instance be determined by solid-state $^{13}$C-NMR measurements in solid hyperpolarised $^{13}$C-lactate, e.g. solid hyperpolarised $^{13}$C-lactate obtained by dynamic nuclear polarisation (DNP) of $^{13}$C-lactate. The solid-state $^{13}$C-NMR measurement according an embodiment consists of a simple pulse-acquire NMR sequence using a low flip angle pulse. The signal intensity of the hyperpolarised $^{13}$C-lactate in the NMR spectrum is compared with signal intensity of $^{13}$C-lactate in a NMR spectrum acquired before the polarisation process. The level of polarisation is then calculated from the ratio of the signal intensities before and after polarisation.

In a similar way, the level of polarisation for dissolved hyperpolarised $^{13}$C-lactate may be determined by liquid state NMR measurements. Again the signal intensity of the dissolved hyperpolarised $^{13}$C-lactate is compared with the signal intensity of the dissolved $^{13}$C-lactate before polarisation or after the polarisation has decayed. The level of polarisation is then calculated from the ratio of the signal intensities of $^{13}$C-lactate before and after polarisation.

Hyperpolarisation of NMR active $^{13}$C-nuclei may be achieved by different methods which are for instance described in WO-A-98/30918, WO-A-99/24080 and WO-A-99/35508, and which all are incorporated herein by reference, and also hyperpolarisation methods known in the art such as polarisation transfer from a noble gas, "brute force", spin refrigeration, the parahydrogen method and dynamic nuclear polarisation (DNP). In an embodiment, DNP is used.

To obtain hyperpolarised $^{13}$C-lactate, according to an embodiment, the $^{13}$C-lactate is polarised directly. Also $^{13}$C-lactic acid may be polarised, however the polarised $^{13}$C-lactic acid needs to be converted to polarised $^{13}$C-lactate, e.g. by neutralisation with a base. $^{13}$C-lactate salts are commercially available, e.g. sodium $^{13}$C-lactate. $^{13}$C-lactic acid is commercially available as well; it can also be obtained by protonating commercially available $^{13}$C-lactate, e.g. commercially available sodium $^{13}$C-lactate.

One way for obtaining hyperpolarised $^{13}$C-lactate is by polarisation transfer from a hyperpolarised noble gas, which is described in WO-A-98/30918. Noble gases having non-zero nuclear spin can be hyperpolarised by the use of circularly polarised light. A hyperpolarised noble gas, in an embodiment He or Xe, or a mixture of such gases, may be used to effect hyperpolarisation of $^{13}$C-nuclei. The hyperpolarised gas may be in the gas phase, it may be dissolved in a liquid/solvent, or the hyperpolarised gas itself may serve as a solvent. Alternatively, the gas may be condensed onto a cooled solid surface and used in this form, or allowed to sublime. In an embodiment, there is an intimate mixing of the hyperpolarised gas with $^{13}$C-lactate or $^{13}$C-lactic acid.

Another way for obtaining hyperpolarised $^{13}$C-lactate is that polarisation is imparted to $^{13}$C-nuclei by thermodynamic equilibration at a very low temperature and high field. Hyperpolarisation compared to the operating field and temperature of the NMR spectrometer is effected by use of a very high field and very low temperature ("brute force"). The magnetic field strength used should be as high as possible, suitably higher than 1 T, in an embodiment higher than 5 T, in an embodiment 15 T or more and in an embodiment 20 T or more. The temperature should be very low, e.g. 4.2 K or less, in an embodiment 1.5 K or less, in an embodiment 1.0 K or less, and in an embodiment 100 mK or less.

Another way for obtaining hyperpolarised $^{13}$C-lactate is the spin refrigeration method. This method covers spin polarisation of a solid compound or system by spin refrigeration polarisation. The system is doped with or intimately mixed with suitable crystalline paramagnetic materials such as $Ni^{2+}$, lanthanide or actinide ions with a symmetry axis of order three or more. The instrumentation is simpler than required for DNP with no need for a uniform magnetic field since no resonance excitation field is applied. The process is carried out by physically rotating the sample around an axis perpendicular to the direction of the magnetic field. The prerequisite for this method is that the paramagnetic species has a highly anisotropic g-factor. As a result of the sample rotation, the electron paramagnetic resonance will be brought into contact with the nuclear spins, leading to a decrease in the nuclear spin temperature. Sample rotation is carried out until the nuclear spin polarisation has reached a new equilibrium.

In an embodiment, DNP (dynamic nuclear polarisation) is used to obtain hyperpolarised $^{13}$C-lactate. Sodium $^{13}$C-lactate is a commercially available compound that may be directly used for DNP since it does not crystallize upon cooling/freezing. Since this eliminates the necessity of glass formers and/or high amounts of solvent(s) in the sample, a highly concentrated sample can be prepared and used in the DNP process. Further, sodium $^{13}$C-lactate samples are pH neutral and hence a variety of DNP agents can be used. In DNP, polarisation of MR active nuclei in a compound to be polarised is effected by a polarisation agent or so-called DNP agent, a compound comprising unpaired electrons. During the DNP process, energy, normally in the form of microwave radiation, is provided, which will initially excite the DNP agent. Upon decay to the ground state, there is a transfer of polarisation from the unpaired electron of the DNP agent to the NMR active nuclei of the compound to be polarised, e.g. to the $^{13}$C nuclei in $^{13}$C-lactate. Generally, a moderate or high magnetic field and a very low temperature are used in the DNP process, e.g. by carrying out the DNP process in liquid helium under vacuum and a magnetic field of about 1 T or above. Alternatively, a moderate magnetic field and any temperature at which sufficient polarisation enhancement is achieved may be employed. The DNP technique is for example further described in WO-A-98/58272 and in WO-A-01/96895, both of which are included by reference herein.

To polarise a chemical entity, i.e. compound, by the DNP method, a composition comprising the compound to be polarised and a DNP agent is prepared which is then frozen and inserted into a DNP polariser for polarisation. After the polarisation, the frozen solid hyperpolarised composition is rapidly transferred into the liquid state, either by melting it or by dissolving it in a suitable dissolution medium. According to an embodiment, there is dissolution, wherein the dissolution process of a frozen hyperpolarised composition and suitable devices therefore are described in detail in WO-A-02/37132. The melting process and suitable devices for the melting are for instance described in WO-A-02/36005.

In order to obtain a high polarisation level in the compound to be polarised said compound and the DNP agent need to be in intimate contact during the DNP process. This is not the case if the composition crystallizes upon being frozen or cooled. To avoid crystallization, either glass formers need to be present in the composition or compounds need to be chosen for polarisation that do not crystallize upon being frozen but rather form a glass. In an embodiment, sodium $^{13}$C-lactate is used since compositions containing sodium $^{13}$C-lactate do not crystallize upon freezing/cooling.

If the hyperpolarised $^{13}$C-$^2$H lactate used in the method of the present invention is obtained by DNP, the sample to be polarised, i.e. $^{13}$C-lactate and a DNP agent may further comprise a paramagnetic metal ion. The presence of paramagnetic metal ions in the composition to be polarised by DNP has found to result in increased polarisation levels in $^{13}$C-lactate, as described in detail in WO-A2-2007/064226, which is incorporated herein by reference. Hence, in an embodiment of the present invention the MR imaging medium comprises [$^{13}$C, $^2$H]lactate, such as [1-$^{13}$C, 2-$^2$H]lactate, a trityl radical and optionally a paramagnetic metal ion. When said paramagnetic metal ion is present this is present in the form of a paramagnetic chelate comprising $Gd^{3+}$. Such MR imaging medium is in an embodiment obtained by dynamic nuclear polarisation.

As mentioned earlier, the imaging medium according to the present invention may be used as imaging medium for in vivo LDH activity determination by $^{13}$C-MR detection, i.e. in living human or non-human animal beings. For this purpose, the imaging medium is provided as a composition that is suitable for being administered to a living human or non-human animal body. Such an imaging medium in an embodiment comprises in addition to the MR active agent, [$^{13}$C, $^2$H]-lactate, an aqueous carrier, in an embodiment a physiologically tolerable and pharmaceutically accepted aqueous carrier like water, a buffer solution or saline. Such an imaging medium may further comprise conventional pharmaceutical or veterinary carriers or excipients, e.g. formulation aids such as are conventional for diagnostic compositions in human or veterinary medicine.

Further, the imaging medium according to the method of the present invention may be used as an imaging medium for in vitro LDH activity determination by $^{13}$C-MR detection, i.e. in cell cultures, body samples such as blood samples, ex vivo tissues such as biopsy tissue or isolated organs. For this purpose, the imaging medium is provided as a composition that is suitable for being added to, for instance, cell cultures, blood samples, ex vivo tissues like biopsy tissue or isolated organs. Such an imaging medium in an embodiment comprises in addition to the MR active agent, $^{13}$C-lactate, a solvent which is compatible with and used for in vitro cell or tissue assays, for instance DMSO or methanol or solvent mixtures comprising an aqueous carrier and a non aqueous solvent, for instance mixtures of DMSO and water or a buffer solution or methanol and water or a buffer solution. As it is apparent for a skilled person, pharmaceutically acceptable carriers, excipients and formulation aids may be present in such an imaging medium but are not required for such a purpose.

If the imaging medium used in the method of the present invention is used for in vivo determination of LDH activity, i.e. in a living human or non-human animal body, said imaging medium is in an embodiment administered to said body parenterally, and in an embodiment, intravenously. Generally, the body under examination is positioned in an MR magnet. Dedicated $^{13}$C-MR and $^1$H-MR, or double-tuned $^{13}$C/$^1$H RF-coils are positioned to cover the area of interest. Exact dosage and concentration of the imaging medium will depend upon a range of factors such as toxicity and the administration route. At less than 400 s after the administration, in an embodiment less than 120 s, or in an embodiment less than 60 s after the administration, an MR imaging sequence is applied, in an embodiment one that encodes the volume of interest in a combined frequency and spatially selective way. The exact time of applying an MR sequence is highly dependent on the volume of interest and the species.

If the imaging medium used in the method of the present invention is used for in vitro determination of LDH activity, said imaging medium is 1 mM to 100 mM in $^{13}$C-lactate, in an embodiment 20 mM to 90 mM and in an embodiment 40 to 80 mM in $^{13}$C-lactate.

In an embodiment of the method of the present invention the LDH-catalysed exchange of deuterium label between [1-$^{13}$C, 2-$^2$H]lactate and endogenous unlabelled lactate is monitored using a heteronuclear $^{13}$C/$^1$H spin echo experiment. In this experiment, in which 180° pulses are applied simultaneously to the $^1$H and $^{13}$C spins and the $^{13}$C resonance is observed, at $\tau=\frac{1}{2}J$, where J is the $^1$H-$^{13}$C coupling constant between the C2 proton and the C1 carbon-13, the $^{13}$C resonance will be inverted. Following LDH-catalysed exchange of deuterium label between the two lactate species, and assuming that both are present at equal concentrations, then there will be, at isotopic equilibrium, an equimolar mixture of [1-$^{13}$C$_1$, 2-$^2$H$_1$]lactate, [1-$^{13}$C$_1$, 2-$^1$H$_1$]lactate, [2-$^2$H$_1$]lactate and [2-$^1$H$_1$]lactate. In the $^{13}$C experiment, only the $^{13}$C-labelled species are observed, and of these [1-$^{13}$C$_1$, 2-$^2$H$_1$] lactate will give a $^{13}$C resonance with positive phase and [1-$^{13}$C$_1$, 2-$^1$H$_1$]lactate a $^{13}$C resonance with negative phase, which will largely cancel. Of course in vivo the concentrations are unlikely to be equal, however the concentration of the [1-$^{13}$C$_1$, 2-$^1$H$_1$]lactate species at any point during the isotope exchange time course can be determined by acquiring heteronuclear spin echo difference spectra obtained in the presence and absence of the 180° $^1$H pulse. Hence in one embodiment of the present invention a method of heteronuclear $^{13}$C/$^1$H spin echo imaging is used to monitor the exchange of deuterium label between [1-$^{13}$C, 2-$^2$H]lactate and endogenous unlabelled lactate.

If the [1-$^{13}$C, 2-$^2$H]lactate isotopomer is used then the $^1$H pulse must be frequency selective in order to avoid phase modulation due to spin-spin coupling between the $^{13}$C nucleus and the C3 methyl protons. The requirement to use a frequency-selective $^1$H pulse is removed if lactate isotopomers are used in which the methyl protons have also been exchanged for deuterium.

In an embodiment of the present invention a hetero-nuclear double echo imaging pulse sequence could be used to detect the C2 protonation state of [1-$^{13}$C, 2-$^2$H]lactate in vivo, in which the echoes are acquired with readout and phase encode gradients in a standard echo planar imaging sequence. $^{13}$C images acquired without the $^1$H pulse will have signal from $^{13}$C-labelled C2 deuterated lactate plus $^{13}$C-labelled C2 protonated lactate and $^{13}$C images acquired with the $^1$H pulse will have signal from $^{13}$C-labelled C2 deuterated lactate minus $^{13}$C-labelled C2 protonated lactate. Addition of these images will give the total $^{13}$C-labelled C2 deuterated lactate and subtraction will give the $^{13}$C-labelled C2 protonated lactate. Hence, in another embodiment of the present invention, heteronuclear double echo imaging is used to monitor the exchange of deuterium label between [1-$^{13}$C, 2-$^2$H]lactate and endogenous unlabelled lactate.

In an embodiment of the method of the present invention, a series of the above-mentioned images are acquired and pixel-by-pixel fitting of signal intensities in images of the C2 protonated and C2 deuterated lactate concentrations are fit to a kinetic model to obtain maps of LDH activity in the tissue. In such, the apparent LDH activity may depend on the rate of delivery of labelled lactate to the tissue, the rate of lactate transport across the cell membrane, and the endogenous lactate concentration. If the method of the present invention is carried out in vivo, i.e. in a living human or non-human animal being, said LDH activity maps may be derived from the whole body, e.g. obtained by whole body in vivo $^{13}$C-MR detection. Alternatively, said LDH activity maps are generated from a region or volume of interest, i.e. a certain tissue, organ or part of said human or non-human animal body.

In an embodiment of the method of the present invention, the above-mentioned signal of $^{13}$C-lactate is used to determine LDH activity of cells in a cell culture, of body samples such as blood samples, of ex vivo tissue like biopsy tissue or of an isolated organ derived from a human or non-human animal being. Said LDH activity is then generated by in vitro $^{13}$C-MR detection.

Thus in an embodiment of the present invention provides a method of determining LDH activity by $^{13}$C-MR detection using an imaging medium comprising hyperpolarised [$^{13}$C, $^2$H]lactate, such as [1-$^{13}$C, 2-$^2$H]lactate, wherein the C2 protonation state is detected and wherein said information is used to generate a map or point measurement of LDH activity.

The LDH activity map or measurement generated in an embodiment of the method according to the present invention is indicative for the LDH activity of the body, part of the body, cells, tissue, body sample etc. under examination and said information obtained may be used in a subsequent step for various purposes.

One of these purposes may be the assessment of compounds that alter LDH activity, in an embodiment, compounds that elevate LDH activity. These might be drugs that improve tissue viability, where one would expect to see an increase in LDH activity.

In an embodiment, the method of the present invention is carried out in vitro and the information obtained is used in assessing the efficacy of potential drugs that alter LDH activity, e.g. in a drug discovery and/or screening process. In such an embodiment, the method of the present invention may be carried out in suitable cell cultures or tissue. The cells or the tissue is contacted with the potential drug and LDH activity is determined by $^{13}$C-MR detection according to the method of the present invention. Information about the efficacy of the potential drug may be obtained by comparing the LDH activity of the treated cells or tissue with the LDH activity of non-treated cells or tissue. Alternatively, the variation of LDH activity may be determined by determining the LDH activity of cells or tissue before and after treatment. Such a drug efficacy assessment may be carried out on for instance microplates, which would allow parallel testing of various potential drugs and/or various doses of potential drugs and thus would make this suitable for high-throughput screening.

In an embodiment, the method of the present invention is carried out in vivo and the information obtained is used in assessing the efficacy of potential drugs that alter LDH activity in vivo. In such an embodiment, the method of the present invention may be carried out in, for instance, test animals or in volunteers in a clinical trial. To the test animal or volunteer a potential drug is administered and LDH activity is determined by $^{13}$C-MR detection according to the method of the present invention. Information about the efficacy of the potential drug may be obtained by determining the variation of LDH activity before and after treatment, e.g. over a certain time period with repeated treatment. Such a drug efficacy assessment may be carried out in pre-clinical research (test animals) or in clinical trials.

In an embodiment, the method of the present invention is carried out in vivo or in vitro and the information obtained is used to assess response to treatment and/or to determine treatment efficacy in diseased patients undergoing treatment for their disease.

As stated earlier the information obtained by the method of the present invention may be used in a subsequent step for various purposes. Another purpose may be to gain insight into disease states, i.e. identifying patients at risk, early detection of diseases, evaluating disease progression, severity and complications related to a disease.

In an embodiment the method of the present invention is carried out in vivo or in vitro and the information obtained is used to monitor progression of a disease. This may be useful for diseases or disorders where the disease has not progressed to a level where treatment is indicated or recommended, e.g. because of severe side-effects associated with said treatment. In such a situation the choice of action is "watchful waiting", i.e. the patient is closely monitored for disease progression and early detection of deterioration. In this embodiment, the method of the present invention may be used to determine the initial LDH activity and to make subsequent LDH activity determinations over a period of time at a certain frequency. It can be expected that a decrease in LDH activity may indicate progress and worsening of a disease and the said decrease can be used by the physician to decide on commencement of treatment. Alternatively, an increase in LDH activity may indicate worsening of disease, for example in cancer, specifically for prostate cancer, there may be increases in LDH and lactate concentration with disease progression, which would increase the apparent LDH activity that is measured by the method of the present invention. To carry out the method of the present invention for the above-mentioned purpose in vitro requires that suitable samples from a patient under treatment are obtainable, e.g. tissue samples or body samples like blood samples.

In an embodiment, the method according to the present invention is used for in vivo MR tumour imaging, tumour therapy monitoring and/or tumour staging of brain tumours, breast tumours, colon tumours, lung tumours, kidney tumours, head and neck tumours, muscle tumours, ovarian tumours, gastric tumours, pancreatic tumours, esophageal tumours and prostate tumours. It has further been found that the method according to the present invention is especially useful for in vivo MR prostate tumour imaging, i.e. prostate tumour diagnosis and/or prostate tumour staging and/or prostate tumour therapy monitoring.

In an embodiment the method of the present invention is carried out in vivo or in vitro and the information obtained is used for determining the severity of a disease. Often diseases progress from their onset over time. Depending on the kind of symptoms and/or the finding of certain clinical markers diseases are characterized by certain stages, e.g. an early (mild) stage, a middle (moderate) stage and a severe (late) stage. More refined stages are common for certain diseases. A variety of clinical markers is known to be used for staging a disease including more specific ones like certain enzymes or protein expression but also more general ones like blood values, electrolyte levels etc. In this context, LDH activity may be such a clinical marker that can be used, alone or in combination with other markers and/or symptoms, to determine a disease stage and thus severity of a disease. Hence it may be possible to use the method of the present invention for determining LDH activity in a patient in a quantitative way and from the LDH activity value obtained staging the patient's disease. LDH ranges which are characteristic for a certain disease stage may be established by determining LDH activity according to the method of the present invention in patients having for instance a disease in an early, middle and late stage and defining a range of LDH activity which is characteristic for a certain stage.

In an embodiment the method of the present invention is carried out in vivo or in vitro and the information obtained is used for identifying and assessing complications related to a disease. With the method of the present invention, LDH activity may be determined in an organ-specific way, for instance by in vivo $^{13}$C-MR detection carried out with surface coils placed over the heart or the kidney.

Anatomical and/or, where suitable, perfusion information may be included in the method of the present invention when carried out in vivo. Anatomical information may for instance be obtained by acquiring a proton or $^{13}$C-MR image with or without employing a suitable contrast agent before or after the method of the present invention.

In an aspect the present invention provides use of an imaging medium comprising hyperpolarized [$^{13}$C, $^2$H]lactate in the determination of LDH activity by $^{13}$C-MR detection.

EXAMPLES

Example 1

Preparation of L-[1-$^{13}$C, 2-$^2$H]Lactate

Sodium L-[1-$^{13}$C$_1$]lactate (250 mg, Cambridge Isotope Laboratories, Andover, Mass., USA) was dissolved in 25 ml 0.02 M sodium phosphate buffer (Fisher Scientific, Loughborough, UK), pH* 5.5 (pH* is the uncorrected pH meter reading) in 99.8% $^2$H$_2$O (Cambridge Isotope Laboratories, Andover, Mass., USA), containing 50 mg EDTA (di-sodium salt, Sigma Aldrich, Gillingham, UK), 10 mg dithiothreitol (Melford Laboratories, Ipswich, UK), 25 mg NAD+ (free acid, Roche Diagnostics, West Sussex, UK), 1 mg (~900 units) rabbit muscle lactate dehydrogenase (Sigma Aldrich, Gillingham, UK) and 5 mg (~30 units) pig heart lipoamide dehydrogenase (lyophilized powder from Calzyme, San Luis Obispo, Calif., USA). The resulting solution was incubated at room temperature for approximately one week. The incubation was terminated by placing the solution in a boiling water bath for 10 min. The precipitated protein was removed by filtration through a 0.22 μm pore size membrane and the zinc salt afforded by acidification of the solution with concentrated hydrochloric acid, followed by neutralization with basic zinc carbonate (Sigma Aldrich, Gillingham, UK). The solution was then filtered, lyophilized and the resulting zinc lactate purified by recrystallisation from a water/ethanol mixture. The sodium salt was prepared using an excess of an ion-exchange resin (Dowex 50Wx8, $Na^+$ form, Sigma Aldrich, Gillingham, UK) and isolated by lyophilization. The lactate was assayed spectrophotometrically in an NADH-linked assay and by $^1H$ NMR spectroscopy.

Example 2

Figure 1B:
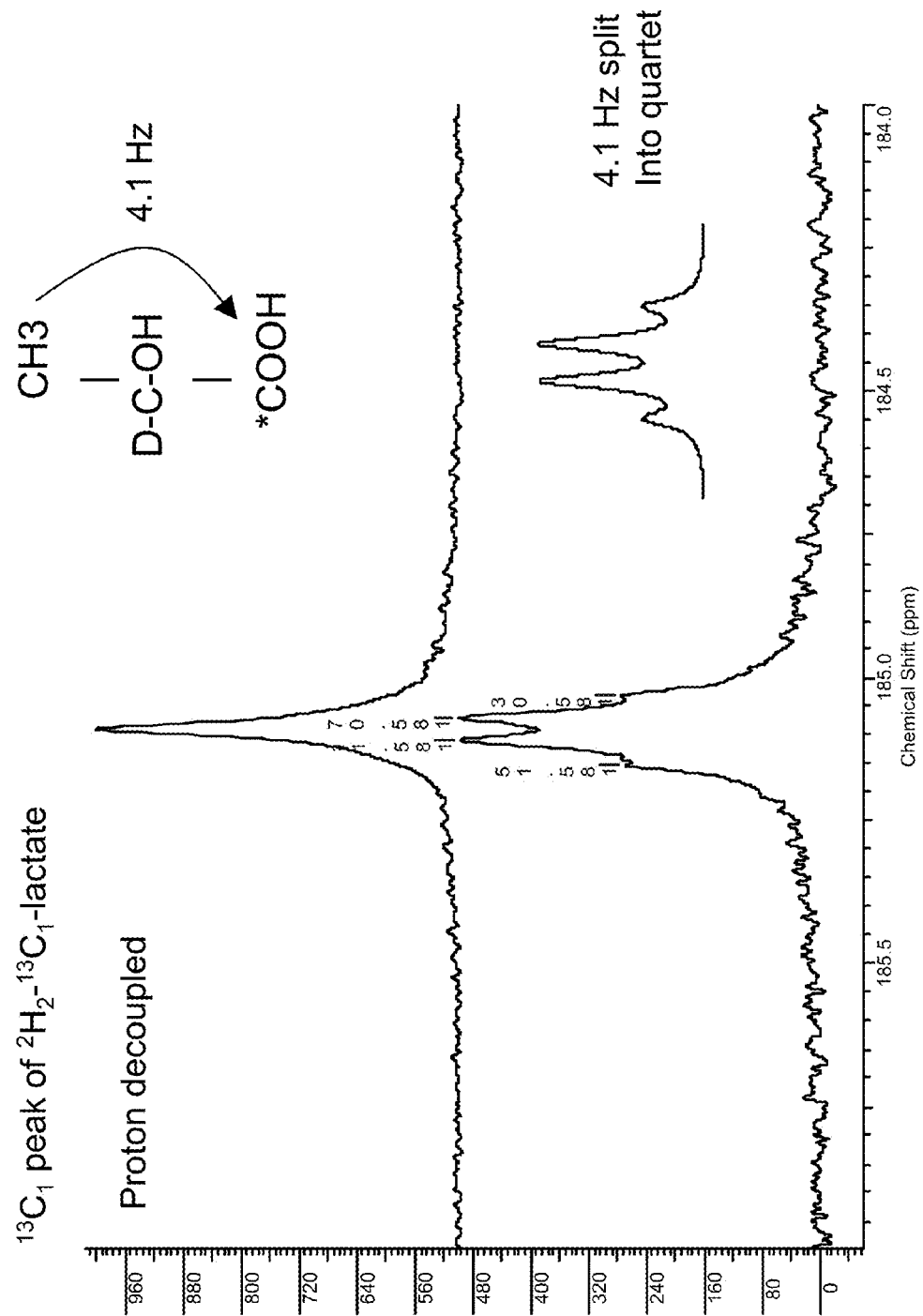

Hetero-Nuclear $^{13}C$ Spin Echo Experiment for Detection of Lactate C2 Protonation The $^{13}C$ spectrum of L-[1-$^{13}C$]lactate shows spin-spin coupling between the C2 proton (J=3.3 Hz) and the C3 methyl protons (J=4.1 Hz). The $^{13}C$ resonance is thus a doublet of quartets (FIG. 1A). Substitution of the C2 proton for deuterium leaves only the spin-spin coupling with the methyl protons (FIG. 1B).

Figure 2:
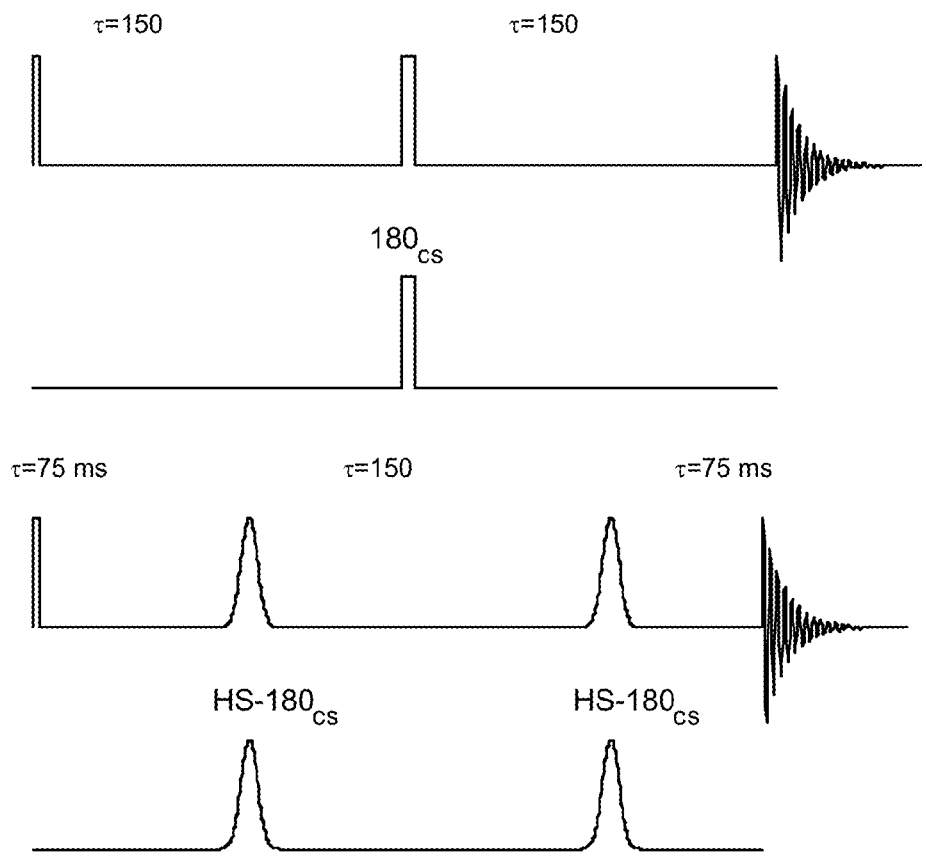
FIG. 2 illustrates hetero-nuclear $^{13}$C/$^1$H spin echo pulse sequences according to an embodiment of the present invention.

A hetero-nuclear $^{13}C/^1H$ spin echo pulse sequence is shown in FIG. 2a). Application of a $^1H$ 180° pulse at the same time as the 180° $^{13}C$ pulse, at τ=½J, results in phase modulation of the observed $^1H$-coupled $^{13}C$ resonances. A double echo sequence (FIG. 2b) was used, since this ensures return of the polarization remaining along the z axis to the +z axis at the end of the experiment.

Figure 3:
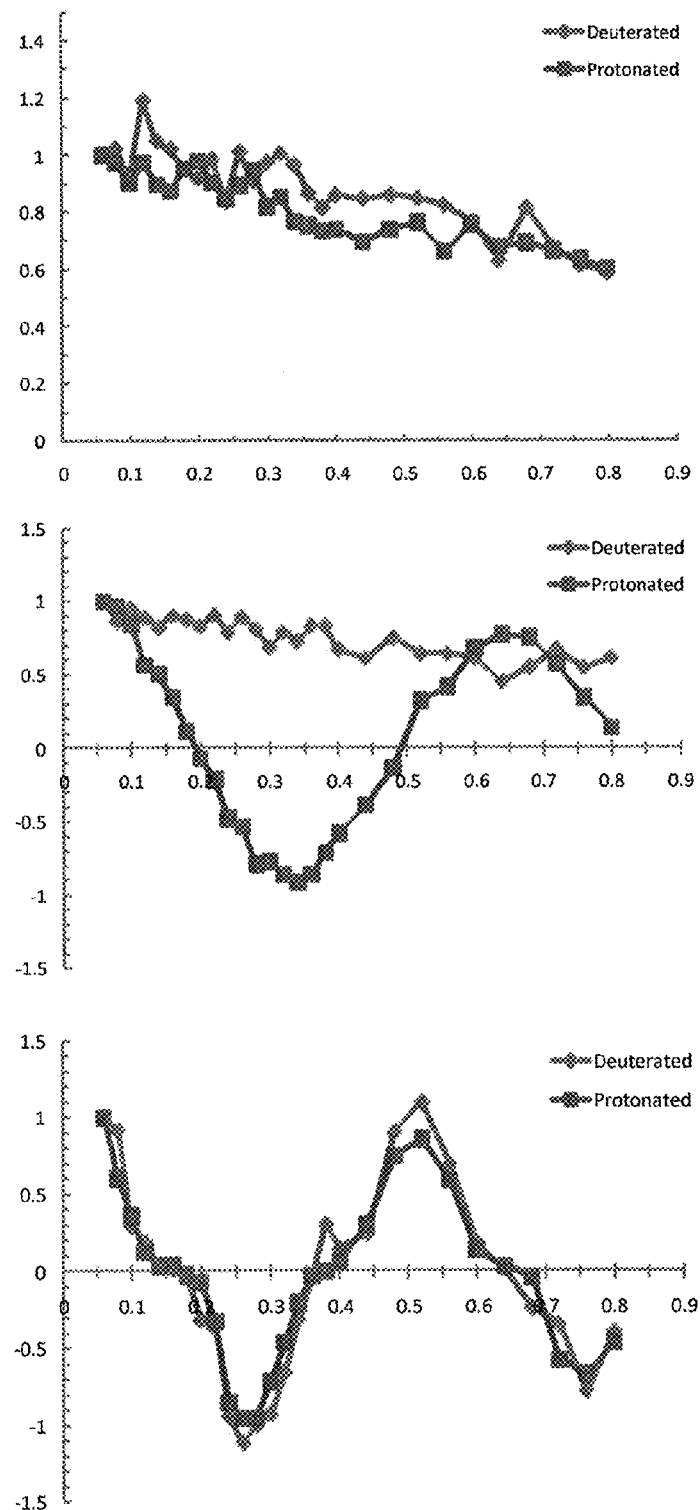
FIG. 3 illustrates C2 proton selective proton pulse resulting in phase inversion of the C1 $^{13}$C resonance according to an embodiment of the present invention.

Acquisition of a hetero-nuclear $^{13}C$ double echo experiment (FIG. 2 b), with a time to echo of 300 ms, and application of a C2-proton selective proton pulse results in phase inversion of the C1 $^{13}C$ resonance (FIG. 3). Similarly, application of a C3-proton selective proton pulse results in phase inversion of the C1 $^{13}C$ resonance (at a time to echo of 240 ms). Substitution of the C2 proton with a deuteron, in L-[1-$^{13}C_1$, 2-$^2H_1$]lactate, removes the phase modulation due to C2 proton coupling (FIG. 3).

For FIG. 3, the samples contained 10 mM of either L-[1-$^{13}C_1$, 2-$^2H_1$]lactate or L-[1-$^{13}C_1$]lactate (non polarized). The $T_1$ of the deuterated lactate was 55.8+/−2.2 s (n=1) and the $T_2$ 1.33+/−0.10 s (n=4) and the $T_1$ of the C2 protonated lactate was 46.9+/−4.0 s (n=1) and the $T_2$ 1.49-/−0.13 s (n=2) (at 9.4 T). Hetero-nuclear $^{13}C/^1H$ double echo spectra were acquired using a 10 μs 90° $^{13}C$ pulse, a 5 ms adiabatic 180° $^{13}C$ pulse (bandwidth ~2 kHz) and a 10 ms adiabatic $^1H$ pulse (bandwidth ~1 kHz), which was centred on either the C2 or C3 lactate proton resonances (FIG. 2b). The TR was 20 s. Initial dummy scans produced a steady state z magnetization. The spectral bandwidth was 8 kHz and data were collected into 2048 complex points. Phase- and amplitude corrected peak integrals for the lactate $^{13}C$ resonance were measured. The echo time is equivalent to 2τ.

Example 3

L-[1-$^{13}C_1$]Lactate with Added $Gd^{3+}$

L-[1-$^{13}C_1$]lactate was hyperpolarized using the DMSO preparation described in (Chen, A. P., et al. Feasibility of using hyperpolarized [1-C-13]lactate as a substrate for in vivo metabolic C-13 MRSI studies. Magnetic Resonance Imaging 26, 721-726 (2008)) with added $Gd^{3+}$. Briefly, 70 mg of a ~50% w/w sodium L-[1-$^{13}C_1$]lactate solution (0.31 mmol) (Sigma Aldrich, Gillingham, UK) is added to 27 mg DMSO (0.36 mmol) (Sigma Aldrich, Gillingham, UK), 2 mg OX 63 radical (1.4 μmol)(GE Healthcare) and 2.7 mg of a 50 mmol/L solution of Dotarem $Gd^{3+}$ chelate (Guerbet, Roissy, France). For in vitro experiments, one third of the resulting solution is polarised to the maximum at the optimal microwave frequency. Once the polarisation is at a maximum, the dissolution is performed with 6 mL of a 40 mmol/L Tris based buffer (pH=7.6) with added 100 mg/L EDTA. The final concentration of hyperpolarised L-[1-$^{13}C_1$]lactate is then approximately 17 mmol/L. Acquisition of hetero-nuclear $^{13}C/^1H$ double echo spectra (TE=300 ms), with and without a 180° $^1H$ pulse, gave the spectra shown in FIG. 4.

Figure 4:
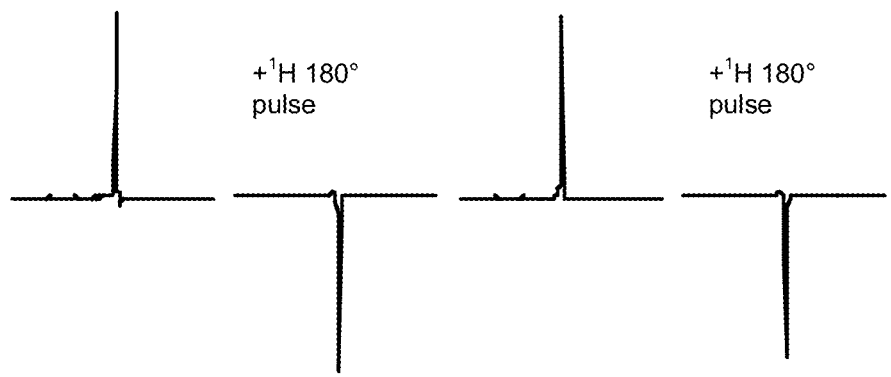
FIG. 4 illustrates hetero-nuclear $^{13}$C/$^2$H double echo spectra according to an embodiment of the present invention.

FIG. 4 shows two successive $^{13}C/^1H$ hetero-nuclear double echo spectra (TE=300 ms) acquired from hyperpolarized L-[1-$^{13}C_1$]lactate using a 1 μs 6° $^{13}C$ pulse, a 5 ms adiabatic 180° $^{13}C$ pulse (bandwidth ~2 kHz) and a 10 ms adiabatic 180° $^1H$ pulse (bandwidth ~1 kHz), which was centred on the C2 lactate proton resonance. Spectra were acquired with and without the 180° $^1H$ pulse. Proton decoupling was applied during the acquisition period. TR=1 sec.

An equimolar mixture of L-[1-$^{13}C_1$]lactate and L-[1-$^{13}C_1$, 2-$^2H_1$]lactate was prepared and polarized to ~26+/−0.5% (n=2). The final lactate concentration in the NMR tube was 10 mM.

Figure 5:
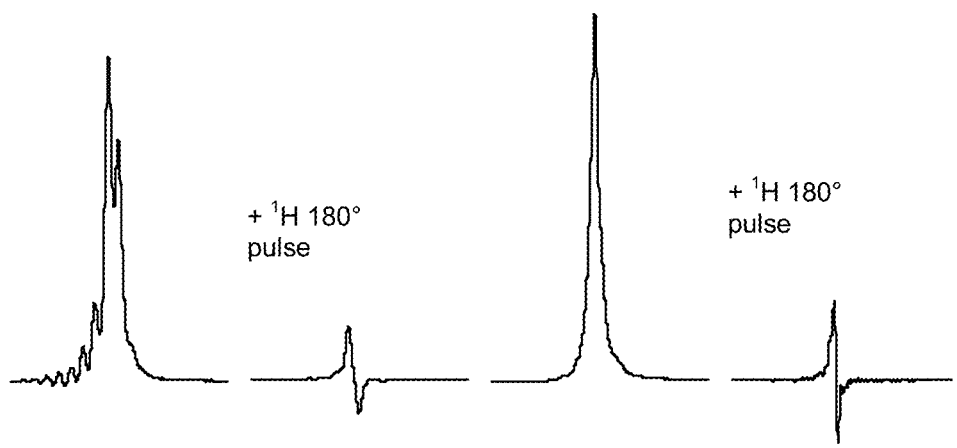
FIG. 5 illustrates heteronuclear $^{13}$C/$^2$H double echo spectra. Mixture of L-[1-$^{13}$C]lactate and L-[1-$^{13}$C, 2-$^2$H$_1$]lactate according to an embodiment of the present invention.

FIG. 5 shows $^{13}C/^1H$ hetero-nuclear spin echo spectra (TE=300 ms) acquired from an equimolar mixture of hyperpolarized L-[1-$^{13}C_1$]lactate and L-[1-$^{13}C_1$, 2-$^2H_1$]lactate using a 1 μs 6° $^{13}C$ pulse, a 5 ms adiabatic 180° $^{13}C$ pulse (bandwidth ~2 kHz) and a 10 ms adiabatic 180° $^1H$ pulse (bandwidth ~1 kHz), which was centred on the C2 lactate proton resonance. Spectra were acquired with and without the 180° $^1H$ pulse. Proton decoupling was applied during the acquisition period where indicated. TR=1 sec.

Figure 6:
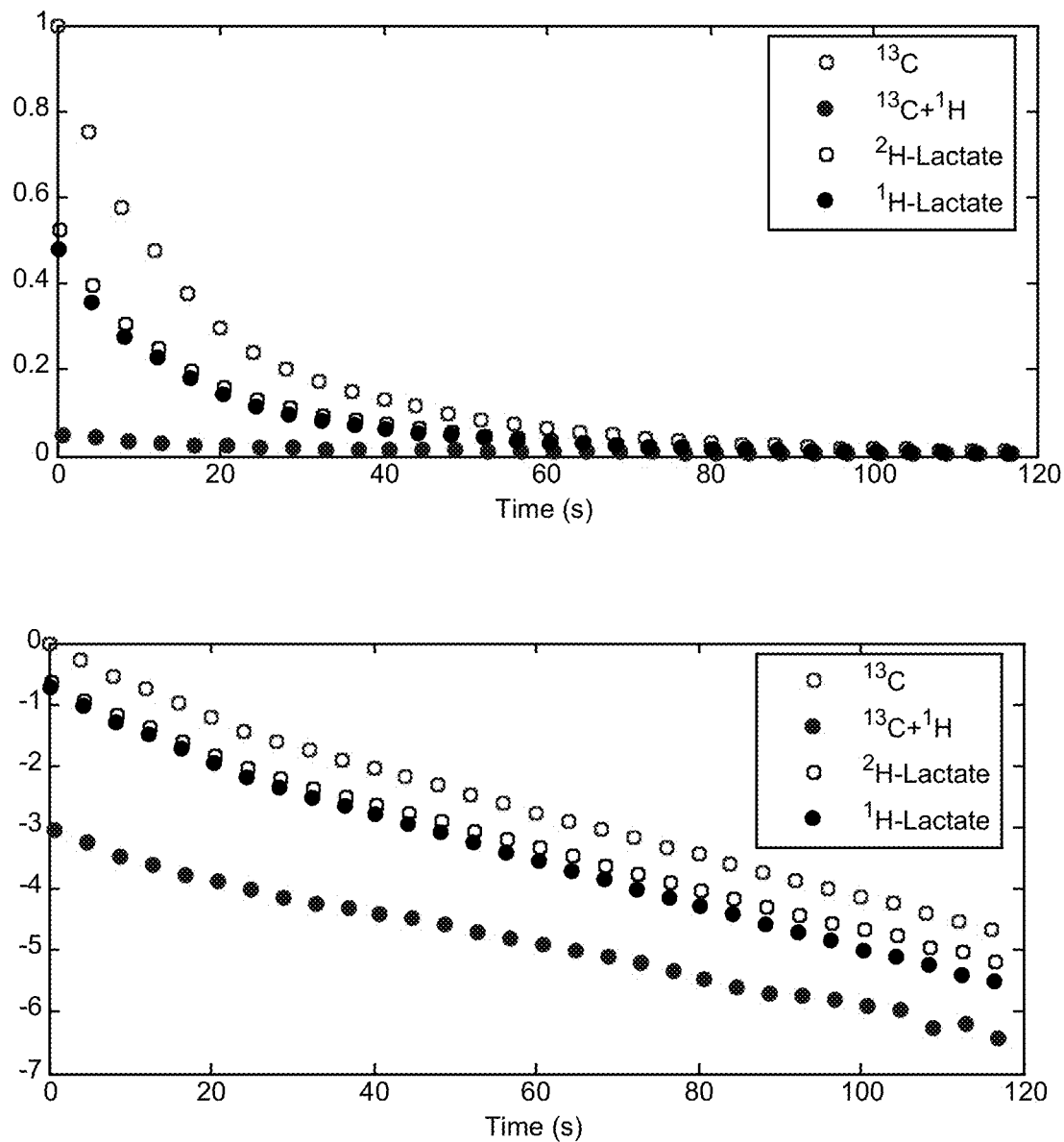
FIG. 6 illustrates multiple heteronuclear $^{13}$C/$^1$H double echo spectra from an equimolar mixture of hyperpolarized L-[1-$^{13}$C]lactate and L-[1-$^{13}$C, 2-2H$_1$]lactate according to an embodiment of the present invention.

Acquisition of a series of these spectra, acquired during the lifetime of the polarization, gave the results shown in FIG. 6. The use of an adiabatic $^{13}C$ pulse ensured that the unsampled $^{13}C$ polarization remained along the z axis. However, the estimated $T_1$s from these data, 27 s for $^2H$-lactate and 25 s for $^1H$-lactate, are much shorter than the $T_1$s estimated for the non-polarized material (FIG. 3) and presumably reflect imperfections in the hyperbolic secant pulses. They may also reflect lack of correction for multiple low flip angle pulses.

Multiple heteronuclear $^{13}C/^1H$ double echo spectra were acquired from an equimolar mixture of hyperpolarized L-[1-$^{13}C_1$]lactate and L-[1-$^{13}C_1$, 2-$^2H_1$]lactate, as described in the legend to FIG. 6. The top plot shows the total $^{13}C$ signal, acquired in the absence of a $^1H$ pulse, the $^{13}C$ signal acquired in the presence of the $^1H$ pulse ($^{13}C+^1H$) and the calculated concentrations of the C2 protonated and deuterated lactate species. The logarithms of these values are shown in the lower plot.

Example 4

In Vivo Experiment Using [1-$^{13}C_1$, 2-$^2H_1$]Lactate

For a hetero-nuclear $^{13}C/^1H$ double echo experiment to detect the C2 protonation state of [1-$^{13}C_1$, 2-$^2H_1$]lactate in vivo, the $^{13}C$ resonance must have sufficiently long $T_1$ and $T_2$.

T₁ Measurements In Vivo

Figure 7:
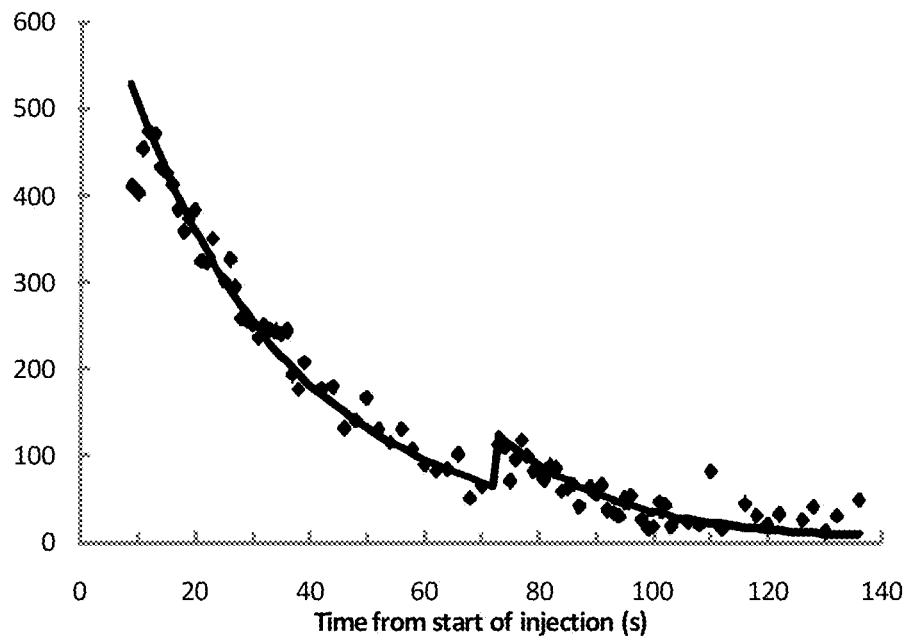
FIG. 7 illustrates a plot of hyperpolarized L-[1-$^{13}$C]lactate signal intensity versus time (in vivo) according to an embodiment of the present invention.

L-[1-$^{13}$C]lactate was polarized as described by Chen, A. P., et al. Feasibility of using hyperpolarized [1-C-13]lactate as a substrate for in vivo metabolic C-13 MRSI studies. *Magnetic Resonance Imaging* 26, 721-726 (2008), and 200 µl injected via a tail vein into an EL4 tumour-bearing mouse. Non-slice selective spectra were collected using a 24-mm diameter surface coil placed over the tumour. An estimated flip angle of 5 degrees and a repetition time (TR) of 1 s were used for the first 32 spectra, which were followed by 16 spectra with a TR of 2 s and then 16 spectra with a flip angle of 10 degrees and a TR of 2 s. The lactate peak integral was plotted as a function of time (FIG. 7) and the data fitted to a model that produced estimates of $T_1$ and flip angle. The lactate $T_1$ in the tumour was estimated to be 33 s (n=1).

T₂ Measurements In Vivo

Figure 8:
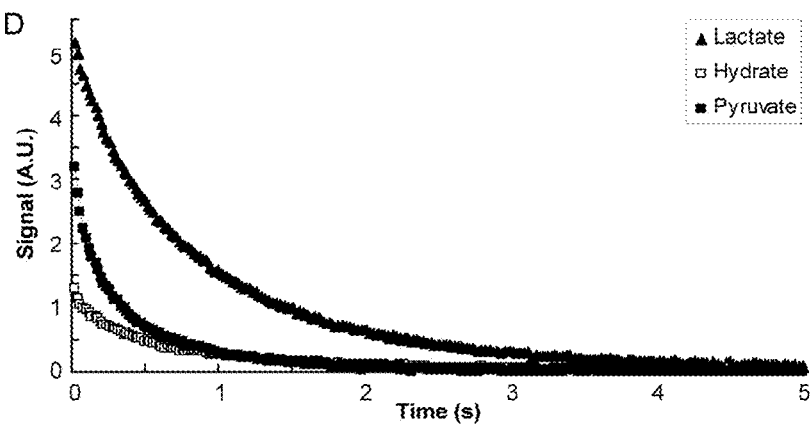
FIG. 8 illustrates decay curve from multi-echo experiment used to estimate $T_2$s in vivo according to an embodiment of the present invention.

The time to echo in the hetero-nuclear spin echo experiment is 300 ms (see FIG. 3), therefore it is essential that the $^{13}$C resonance has a long $T_2$. We have previously measured transverse relaxation times for [1-$^{13}$C]lactate in EL4 lymphoma tumors in vivo at 9.4 T following injection of [1-$^{13}$C] pyruvate, see Kettunen, M. I., et al. Magnetization transfer measurements of exchange between hyperpolarized [1-$^{13}$C] pyruvate and [1-$^{13}$C]lactate in a murine lymphoma. *Magn Reson Med* 63, 872-880 (2010). Multi-exponential $T_2$ relaxation was observed for both the lactate and pyruvate resonances (FIG. 8).

Figure 9:
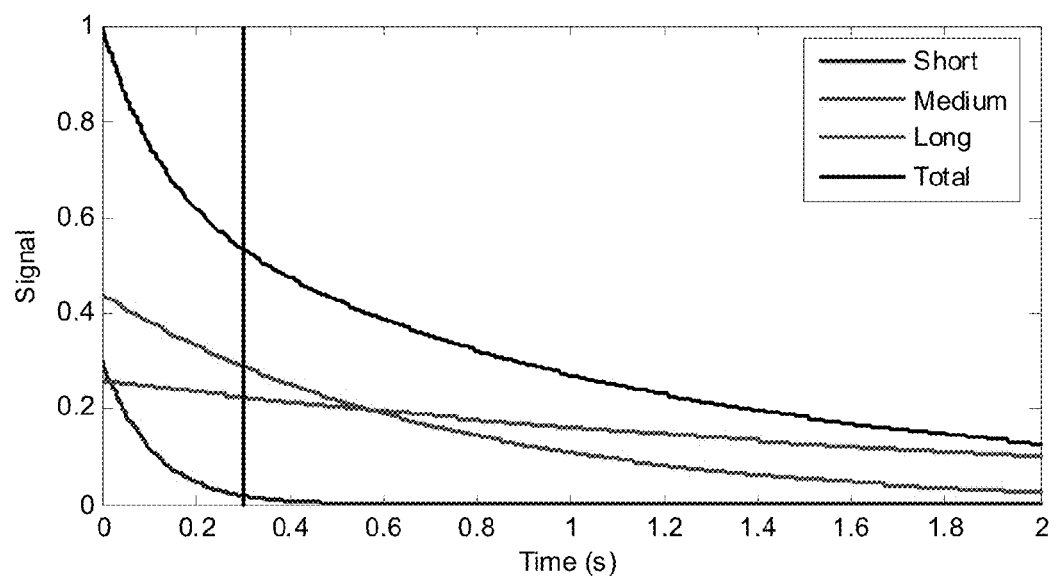
FIG. 9 illustrates the contribution of different $T_2$ components to the lactate signal as a function of echo time in vivo according to an embodiment of the present invention.

For lactate (n=8), three components were fitted to the experimental data (FIG. 9), a short $T_2$ component (0.13±0.09 s, 31±21%), a medium $T_2$ component (0.75±0.20 s, 52±16%) and a long $T_2$ component (2.2±0.7 s, 23±15%). Similar multi-exponential behavior has also been reported at 3 T, see Yen, Y., et al. Signal Enhancement in Low-Dose Hyperpolarized $^{13}$C Imaging Using Multi-Slice FSEPSI Sequence, in *Proc Intl Soc Mag Res Med*, Vol. 16 890 (Toronto, 2008).

Therefore with an echo time of 300 ms, nearly 60% of the total [1-$^{13}$C]lactate signal will remain.

In a hetero-nuclear double echo imaging pulse sequence, which could be used to detect the C2 protonation state of [1-$^{13}$C, 2-$^2$H]lactate in vivo, the echoes will be acquired with readout and phase encode gradients in a standard EPI sequence. By using adiabatic $^{13}$C pulses we ensure that the unsampled $^{13}$C polarization remains along the z axis and by using a double echo sequence we ensure that this polarization is returned to the +z axis at the end of the pulse sequence. The $^1$H pulse will be switched off resonance on alternate acquisitions, which will turn off phase modulation of the $^{13}$C signal on alternate acquisitions (see FIG. 3). $^{13}$C images acquired without the $^1$H pulse will have signal from $^{13}$C-labelled C2 deuterated lactate plus $^{13}$C-labelled C2 protonated lactate and $^{13}$C images acquired with the $^1$H pulse will have signal from $^{13}$C-labelled C2 deuterated lactate minus $^{13}$C-labelled C2 protonated lactate. Addition of these images will give the total $^{13}$C-labelled C2 deuterated lactate and subtraction will give the Re-labelled C2 protonated lactate.

What is claimed is:

1. A MR imaging medium comprising a hyperpolarised [$^{13}$C, $^2$H]lactate isotopomer.

2. The MR imaging medium according to claim 1, wherein the [$^{13}$C, $^2$H]lactate isotopomer is selected from the group of [1-$^{13}$C, 2-$^2$H]lactate, [2-$^{13}$C, 2-$^2$H]lactate, [3-$^{13}$C, 2-$^2$H]lactate, [1-$^{13}$C, 2,3-$^2$H]lactate, [2-$^{13}$C, 2,3-$^2$H]lactate and [3-$^{13}$C, 2,3-$^2$H]lactate.

3. The MR imaging medium according to claim 1, wherein more than one of the C1, C2 and C3 positions of the [$^{13}$C, $^2$H]lactate isotopomer are $^{13}$C labelled and wherein the C2 position, or the C2 and C3 positions, are deuterium labelled.

4. The MR imaging medium according to claim 1, further comprising a trityl radical and optionally a paramagnetic metal ion.

5. The MR imaging medium according to claim 4, wherein the paramagnetic metal ion is present and is a paramagnetic chelate comprising $Gd^{3+}$.

6. The MR imaging medium according to claim 1, wherein the hyperpolarised [$^{13}$C, $^2$H]lactate isotopomer is obtained by dynamic nuclear polarisation.

7. A magnetic resonance imaging medium comprising a hyperpolarised [$^{13}$C, $^2$H]lactate isotopomer,
wherein the [13C, 2H]lactate isotopomer is selected from the group of [1-$^{13}$C, 2-$^2$H]lactate, [2-$^{13}$C, 2-$^2$H]lactate, [1-$^{13}$C, 2,3-$^2$H]lactate, and [2-$^{13}$C, 2,3-$^2$H]lactate.

8. A magnetic resonance imaging medium comprising a hyperpolarised [$^{13}$C, $^2$H]lactate isotopomer,
wherein the [13C, 2H]lactate isotopomer is selected from the group of [1-$^{13}$C, 2-$^2$H]lactate, [2-$^{13}$C, 2-$^2$H]lactate, [1-$^{13}$C, 2,3-$^2$H]lactate, and [2-$^{13}$C, 2,3-$^2$H]lactate;
wherein the medium further comprises a trityl radical and optionally a paramagnetic metal ion.

* * * * *

UNITED STATES PATENT AND TRADEMARK OFFICE
CERTIFICATE OF CORRECTION

PATENT NO. : 9,259,490 B2
APPLICATION NO. : 13/695872
DATED : February 16, 2016
INVENTOR(S) : Brindle et al.

It is certified that error appears in the above-identified patent and that said Letters Patent is hereby corrected as shown below:

On the Title Page,

In item (75), under "Inventors", in Column 1, Line 1, delete "Kevin Brindle," and insert -- Kevin M. Brindle, --, therefor.

On Page 2, in item (56), under "OTHER PUBLICATIONS", in Column 1, Line 1, delete "L-[2-2H, 2-13 C]" and insert -- L-[2-$^{2}$H, 2-$^{13}$C] --, therefor.

On Page 2, in item (56), under "OTHER PUBLICATIONS", in Column 1, Line 2, delete "D-[2-13C] glucose in the presence of H2O," and insert -- D-[2-$^{13}$C] glucose in the presence of H$_2$O, --, therefor.

On Page 2, in item (56), under "OTHER PUBLICATIONS", in Column 2, Line 10, delete "13C" and insert -- $^{13}$C --, therefor.

On Page 2, in item (56), under "OTHER PUBLICATIONS", in Column 2, Line 13, delete "[1-C-13]" and insert -- [1-$^{13}$C] --, therefor.

On Page 2, in item (56), under "OTHER PUBLICATIONS", in Column 2, Line 16, delete "13C" and insert -- $^{13}$C --, therefor.

On Page 2, in item (56), under "OTHER PUBLICATIONS", in Column 2, Line 21, delete "[1-13C]Pyruvate and [1-13C]Lactate" and insert -- [1-$^{13}$C]Pyruvate and [1-$^{13}$C]Lactate --, therefor.

In the Specification

In Column 2, Line 54, delete "[3-$^{2}$H$_3$, 2-$^{2}$$_1$]" and insert -- [3-$^{2}$H$_3$, 2-$^{2}$H$_1$] --, therefor.

In Column 3, Line 44, delete "$^{13}$C/$^{2}$H" and insert -- $^{13}$C/$^{1}$H --, therefor.

Signed and Sealed this
Twenty-sixth Day of July, 2016

Michelle K. Lee
*Director of the United States Patent and Trademark Office*

CERTIFICATE OF CORRECTION (continued)
U.S. Pat. No. 9,259,490 B2

In Column 3, Line 46, delete "$^{13}C/^{2}H$" and insert -- $^{13}C/^{1}H$ --, therefor.

In Column 3, Line 51, delete "L-[1-$^{13}$C, 2-2H$_1$]" and insert -- L-[1-$^{13}$C, 2-$^2$H$_1$] --, therefor.

In Column 4, Line 66, delete "[13C, 2H] lactate and endogeneous" and insert -- [$^{13}$C, $^2$H] lactate and endogeneous --, therefor.

In Column 14, Line 7, delete "[1-C-13] lactate" and insert -- [1-$^{13}$C] lactate --, therefor.

In Column 15, Line 3, delete "[1-C-13] lactate" and insert -- [1-$^{13}$C] lactate --, therefor In Column 16, Line 10, delete "Re-labelled C2" and insert -- $^{13}$C-labelled C2 --, therefor.

In the Claims

In Column 16, Line 35, in Claim 7, delete "[13C, 2H]" and insert -- [$^{13}$C, $^2$H] --, therefor.

In Column 16, Line 40, in Claim 8, delete "[13C, 2H]" and insert -- [$^{13}$C, $^2$H] --, therefor.